United States Patent
Barker

(10) Patent No.: US 8,301,255 B2
(45) Date of Patent: Oct. 30, 2012

(54) RETENTION ASSEMBLIES FOR IMPLANTABLE ELECTRIC STIMULATION SYSTEMS AND METHODS OF MAKING AND USING

(75) Inventor: John Michael Barker, Ventura, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 536 days.

(21) Appl. No.: 12/507,692

(22) Filed: Jul. 22, 2009

(65) Prior Publication Data

US 2010/0042169 A1 Feb. 18, 2010

Related U.S. Application Data

(60) Provisional application No. 61/088,301, filed on Aug. 12, 2008.

(51) Int. Cl.
*A61N 1/00* (2006.01)
(52) U.S. Cl. ............. 607/37; 607/38; 607/116; 604/538
(58) Field of Classification Search ............. 607/37–38, 607/116; 604/538
See application file for complete search history.

(56) References Cited

U.S. PATENT DOCUMENTS

| | | | |
|---|---|---|---|
| 4,784,141 A | 11/1988 | Peers-Trevarton | |
| 5,036,862 A | 8/1991 | Pohndorf | |
| 5,246,014 A | 9/1993 | Williams et al. | |
| 5,257,622 A | 11/1993 | Hooper et al. | |
| 5,439,391 A | 8/1995 | McEtchin et al. | |
| 6,006,135 A | 12/1999 | Kast et al. | |
| 6,181,969 B1 | 1/2001 | Gord | |
| 6,205,358 B1 | 3/2001 | Haeg et al. | |
| 6,428,368 B1 | 8/2002 | Hawkins et al. | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,671,534 B2 * | 12/2003 | Putz ............................... 600/378 | |
| 6,705,900 B2 | 3/2004 | Sommer et al. | |
| 6,741,892 B1 | 5/2004 | Meadows et al. | |
| 6,755,694 B2 | 6/2004 | Ries et al. | |
| 6,854,994 B2 | 2/2005 | Stein et al. | |
| 6,921,295 B2 | 7/2005 | Sommer et al. | |

(Continued)

FOREIGN PATENT DOCUMENTS

EP 618822 A1 10/1994

(Continued)

OTHER PUBLICATIONS

U.S. Appl. No. 11/238,240, filed Sep. 29, 2005 (20 pgs.).

*Primary Examiner* — Nicole F Lavert
(74) *Attorney, Agent, or Firm* — Frommer Lawrence & Haug LLP; Patrick R. Turner

(57) ABSTRACT

A connector assembly includes a lead or a lead extension, a connector, and a retention assembly disposed in the connector. The connector includes a connector housing defining a port at a distal end of the connector, and a plurality of connector contacts disposed in the connector housing. The port is configured and arranged for receiving a proximal end of the lead or the lead extension. The connector contacts are configured and arranged to couple to at least one terminal disposed on the proximal end of the lead or the lead extension. The retention assembly includes a retention mechanism that can be engaged and reversibly disengaged without the use of tools beyond conventional operating-room surgical instruments.

11 Claims, 11 Drawing Sheets

U.S. PATENT DOCUMENTS

| | | | |
|---|---|---|---|
| 7,035,689 B1 | 4/2006 | Hawkins et al. |
| 7,231,253 B2 | 6/2007 | Tidemand et al. |
| 7,241,180 B1 | 7/2007 | Rentas Torres |
| 7,244,150 B1 | 7/2007 | Brase et al. |
| 7,287,995 B2 | 10/2007 | Stein et al. |
| 7,305,267 B2 | 12/2007 | Hector |
| 2001/0034543 A1 | 10/2001 | Haeg et al. |
| 2002/0115343 A1 | 8/2002 | Sommer et al. |
| 2003/0073348 A1 | 4/2003 | Ries et al. |
| 2003/0077935 A1 | 4/2003 | Stein et al. |
| 2003/0114905 A1 | 6/2003 | Kuzma |
| 2003/0143895 A1 | 7/2003 | Sommer et al. |
| 2004/0122481 A1 | 6/2004 | Tidemand et al. |
| 2004/0215282 A1 | 10/2004 | Weijden et al. |
| 2005/0033371 A1 | 2/2005 | Sommer et al. |
| 2005/0065570 A1 | 3/2005 | Stein et al. |
| 2005/0131483 A1 | 6/2005 | Zhao et al. |
| 2005/0165465 A1 | 7/2005 | Pianca et al. |
| 2005/0171509 A1* | 8/2005 | Hector ........................ 604/533 |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0178770 A1 | 8/2007 | Rentas Torres |
| 2007/0219595 A1 | 9/2007 | He |
| 2007/0239243 A1 | 10/2007 | Moffitt et al. |
| 2008/0039900 A1 | 2/2008 | Stein et al. |
| 2008/0071320 A1 | 3/2008 | Brase |
| 2008/0139031 A1 | 6/2008 | Ries et al. |
| 2008/0139053 A1 | 6/2008 | Ries et al. |
| 2008/0255630 A1 | 10/2008 | Arisso et al. |
| 2008/0262564 A1 | 10/2008 | Alexander et al. |
| 2009/0222073 A1 | 9/2009 | Flowers et al. |

FOREIGN PATENT DOCUMENTS

| | | | |
|---|---|---|---|
| EP | 1017449 A1 | 7/2000 |
| WO | 9305844 A1 | 4/1993 |
| WO | 9308871 A1 | 5/1993 |
| WO | 9916503 A1 | 4/1999 |
| WO | 02068050 A1 | 9/2002 |
| WO | 03059439 A2 | 7/2003 |
| WO | 2004047910 A2 | 6/2004 |
| WO | 2004060484 A2 | 7/2004 |
| WO | 2005016451 A1 | 2/2005 |
| WO | 2007089974 A2 | 8/2007 |
| WO | 2008070836 A1 | 6/2008 |
| WO | 2008130819 A2 | 10/2008 |

* cited by examiner

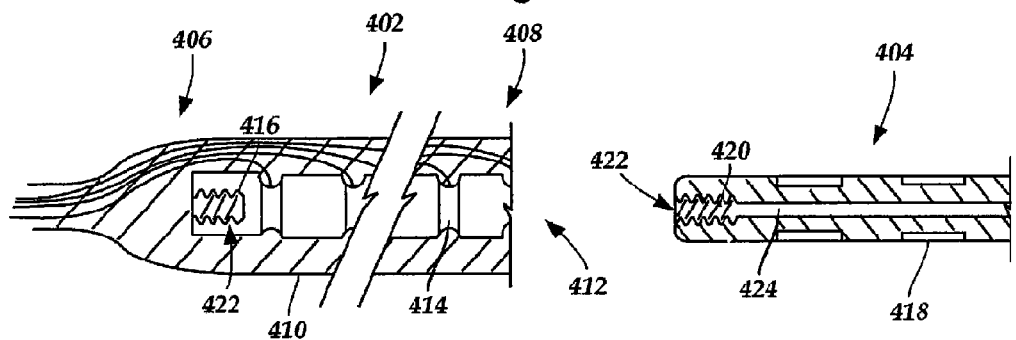
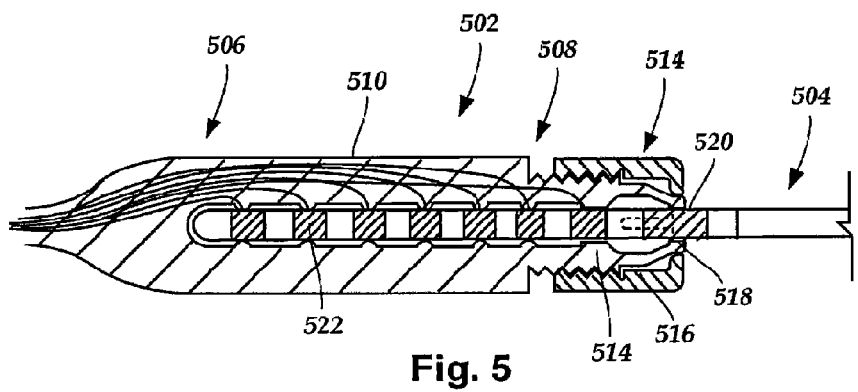

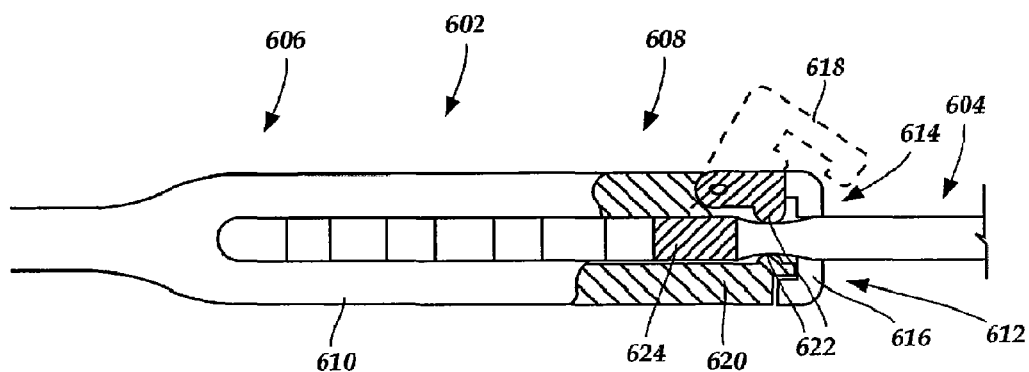
Fig. 6
Fig. 7A
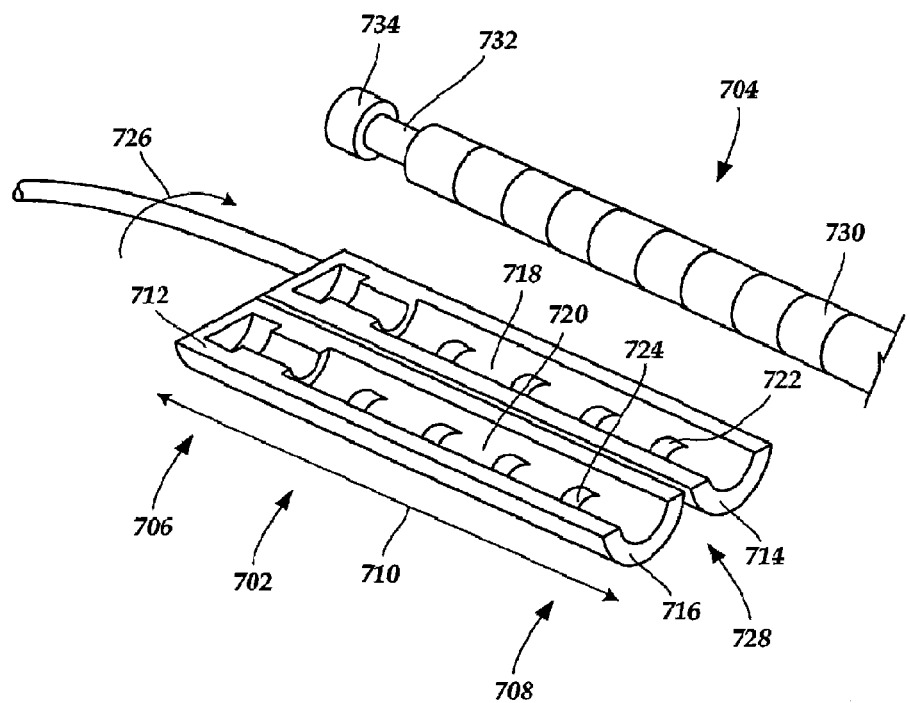

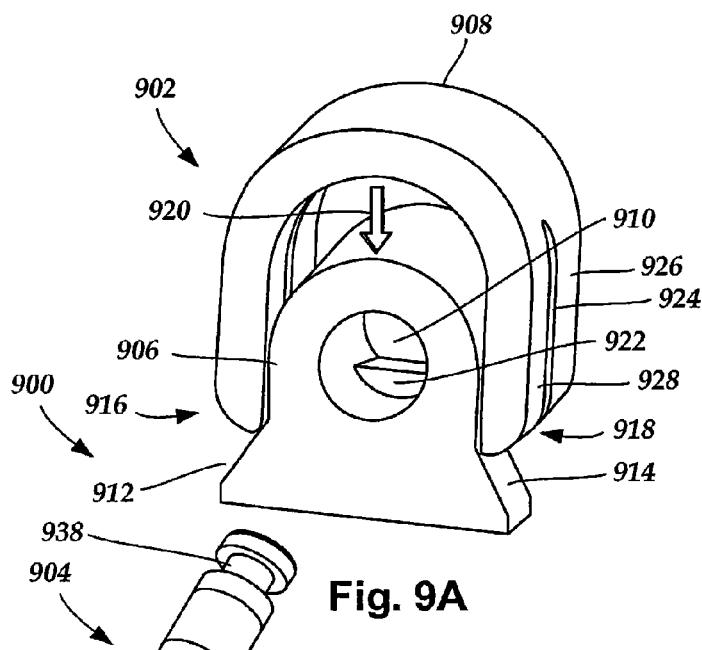
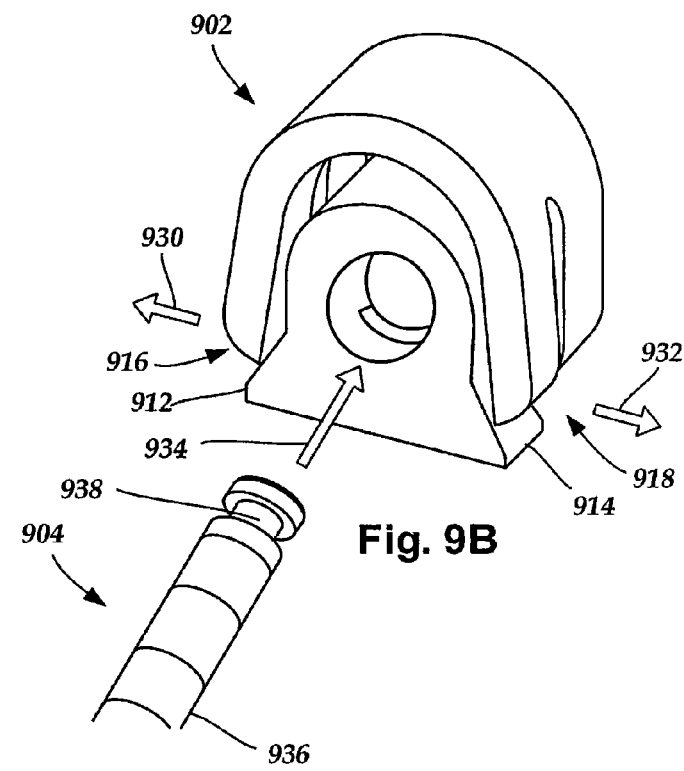

RETENTION ASSEMBLIES FOR IMPLANTABLE ELECTRIC STIMULATION SYSTEMS AND METHODS OF MAKING AND USING

CROSS-REFERENCE TO RELATED APPLICATIONS

This application is a utility patent application based on a previously filed U.S. Provisional Patent Application, Ser. No. 61/088,301 filed on Aug. 12, 2008, the benefit of which is hereby claimed under 35 U.S.C. §119(e) and incorporated herein by reference.

TECHNICAL FIELD

The present invention is directed to the area of implantable electrical stimulation systems and methods of making and using the systems. The present invention is also directed to implantable electrical stimulation systems having leads or lead extensions secured to connectors by retention assemblies, as well as methods of making and using retention assemblies, leads, lead extensions, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a connector assembly includes a lead or a lead extension, a connector, and a retention assembly disposed in the connector. The lead or the lead extension includes a proximal end and an outer covering. The lead or the lead extension also includes a plurality of terminals disposed at the proximal end of the lead or the lead extension. The connector includes a proximal end, a distal end, and a longitudinal length and is configured and arranged to receive the lead or the lead extension. The connector also includes a connector housing defining a port at the distal end of the connector, and a plurality of connector contacts disposed in the connector housing. The port is configured and arranged for receiving the proximal end of the lead or the lead extension. The connector contacts are configured and arranged to couple to at least one of the plurality of terminals disposed on the proximal end of the lead or the lead extension. The retention assembly is configured and arranged for removably securing the lead or the lead extension to the connector. The retention assembly includes a threaded member disposed on either i) the connector or ii) the lead or the lead extension that is configured and arranged to mate with a threaded aperture defined in the other of i) the connector or ii) the lead or the lead extension.

In another embodiment, a connector assembly includes a lead or a lead extension and a connector. The lead or the lead assembly includes a proximal end and an outer covering. The lead or the lead extension also includes a plurality of terminals disposed at the proximal end of the lead or the lead extension and an annular groove disposed in the proximal end of the lead or the lead extension. The connector includes a proximal end, a distal end, and a longitudinal length and is configured and arranged to receive the lead or the lead extension. The connector also includes a connector housing, a plurality of connector contacts, and a retention assembly. The connector housing defines a port at the distal end of the connector. The port is configured and arranged for receiving the proximal end of the lead or the lead extension. The plurality of connector contacts are disposed in the connector housing and are configured and arranged to couple to at least one of the plurality of terminals disposed on the proximal end of the lead or the lead extension. The retention assembly is configured and arranged for removably securing the lead or the lead extension to the connector. The retention assembly includes a coupling member disposed on the connector. The coupling member is configured and arranged to couple with the annular groove disposed in the lead or the lead extension.

In yet another embodiment, a connector assembly includes a lead or a lead extension and a connector. The lead or the lead extension includes a proximal end and an outer covering. The lead or the lead extension also includes a plurality of terminals disposed at the proximal end of the lead or the lead extension. The connector includes a proximal end, a distal end, and a longitudinal length and is configured and arranged to receive the lead or the lead extension. The connector also includes a connector housing, a plurality of connector contacts, and a retention assembly. The connector housing defines a port at the distal end of the connector. The port is configured and arranged for receiving the proximal end of the lead or the lead extension. The plurality of connector contacts are disposed in the connector housing. The connector contacts are configured and arranged to couple to at least one of the plurality of terminals disposed on the proximal end of the lead or the lead extension. The retention assembly is disposed in the connector. The retention assembly includes at least one retention member. The retention assembly is configured and arranged for removably securing the lead or the lead extension to the connector by bending or pivoting the at least one retention member to press against the lead or the lead extension.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4 is a schematic longitudinal cross-sectional view of one embodiment of a connector that includes a threaded post and a proximal end of a lead or a lead extension defining a threaded aperture configured and arranged to mate with the threaded post, according to the invention;

FIG. 5 is a schematic longitudinal cross-sectional view of one embodiment of a connector that includes a threaded collar and a split collet and a proximal end of a lead or a lead extension that includes a retention sleeve, the proximal end of the lead or the lead extension secured in the connector by the split collet pressing against the retention sleeve, according to the invention;

FIG. 6 is a schematic side view of a one embodiments of a connector that includes a locking lever shown in two positions, with a portion of the connector shown as a longitudinal cross-sectional view of the connector with a proximal end of a lead or a lead extension that includes a retention sleeve inserted into the connector, the proximal end of the lead or the lead extension secured in the connector by the locking lever pressing against the body of the lead or the lead extension distal to the retention sleeve, according to the invention;

FIG. 7A is a schematic perspective view of a connector that includes a split shell connector housing in an open position and a proximal end of a lead or a lead extension configured and arranged for insertion into the split shell connector housing, according to the invention;

FIG. 9A is a schematic perspective view of one embodiment of a retention assembly that includes a sliding lock configured and arranged to be mounted to a connector, the sliding lock in a retaining position, and a proximal end of a lead or a lead extension configured and arranged for insertion into the sliding lock, according to the invention;

FIG. 9B is a schematic perspective view of one embodiment of the sliding lock shown in FIG. 9A in an open position and a proximal end of a lead or a lead extension configured and arranged for insertion into the sliding lock, according to the invention;

DETAILED DESCRIPTION

The present invention is directed to the area of implantable electrical stimulation systems and methods of making and using the systems. The present invention is also directed to implantable electrical stimulation systems having leads or lead extensions secured to connectors by retention assemblies, as well as methods of making and using retention assemblies, leads, lead extensions, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741, 892; and U.S. Patent Application Publications Nos. 2003/ 0114905; 2005/0165465; 2007/0150036; 2007/0161294; 2007/0219595; 2007/0239243; and 2007/0150007; U.S. patent application Ser. No. 11/238,240; all of which are incorporated by reference.

Figure 1:
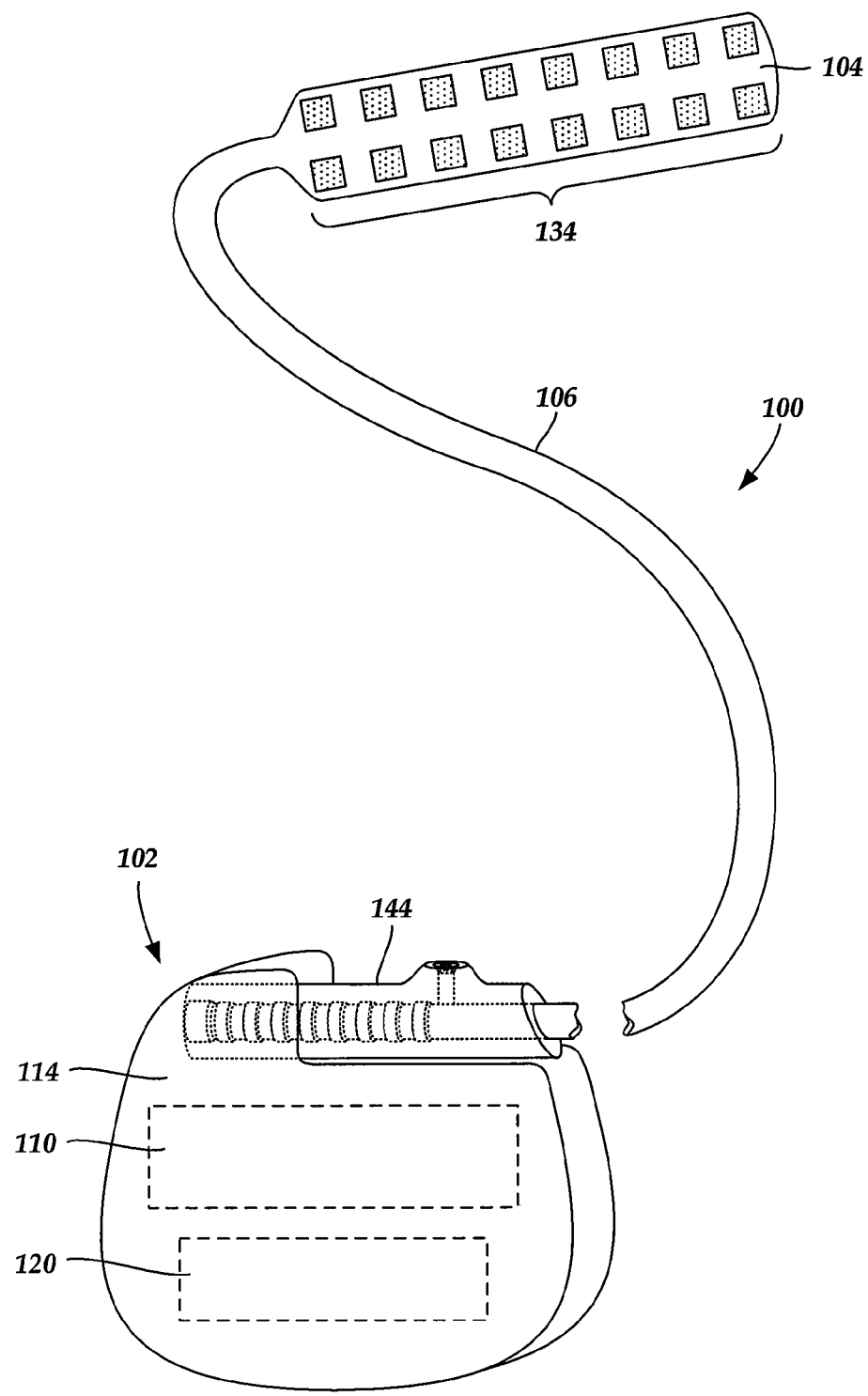
FIG. 1 is a schematic view of one embodiment of an electrical stimulation system, according to the invention.
Figure 2:
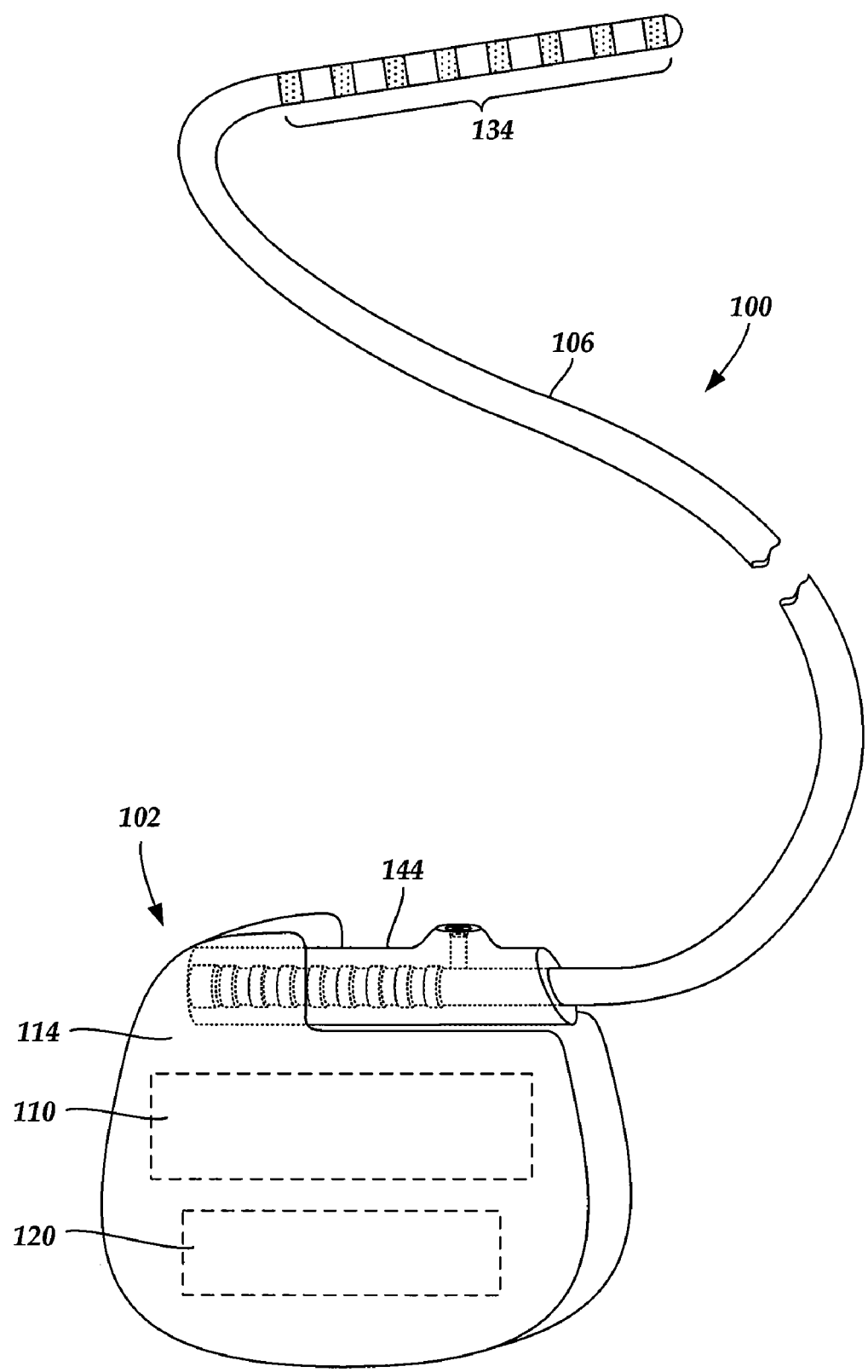
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires (not shown) extend from the terminals (e.g., 310 in FIG. 3A and 336 of FIG. 3B) to the electrodes 134. In some embodiments, each terminal (e.g., 310 in FIG. 3A and 336 of FIG. 3B) is connected to one electrode 134. In other embodiments, each terminal (e.g., 310 in FIG. 3A and 336 of FIG. 3B) is connected to a plurality of electrodes 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
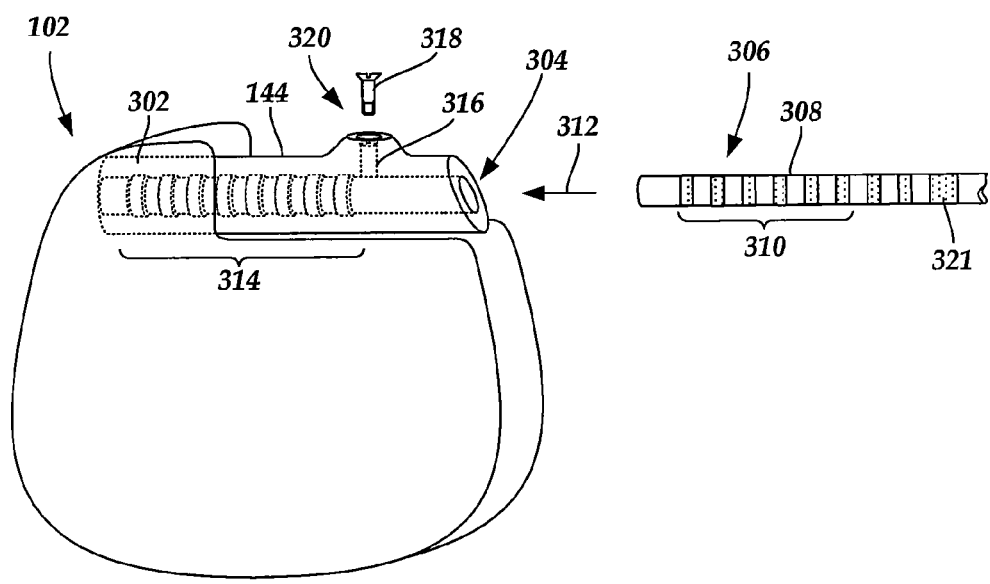
FIG. 3A is a schematic view of one embodiment of a proximal portion of a lead and a control module of an electrical stimulation system, according to the invention.
Figure 3B:
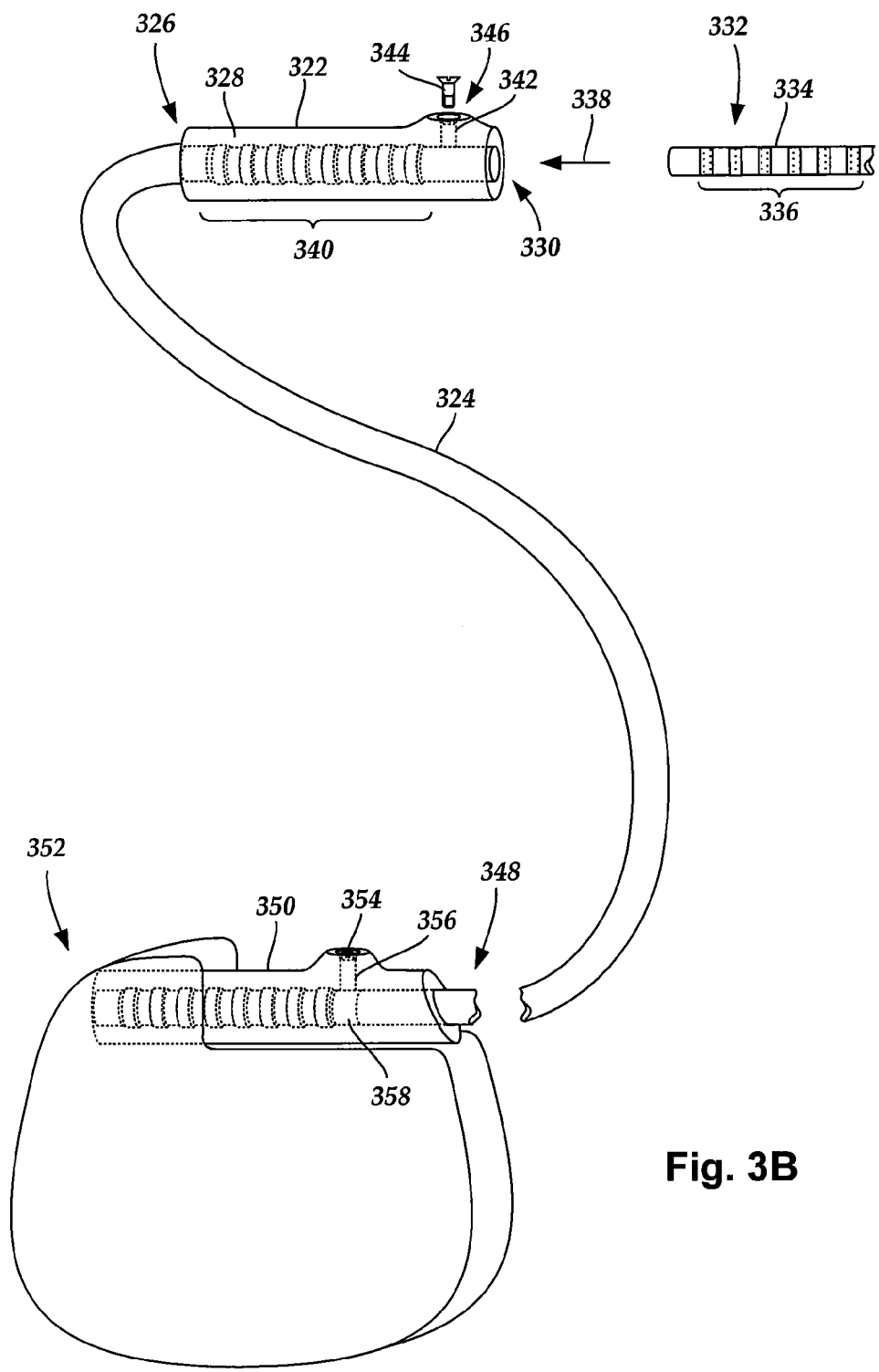
FIG. 3B is a schematic view of one embodiment of a proximal portion of a lead and a lead extension of an electrical stimulation system, according to the invention.

Retention assemblies are sometimes used to secure two or more coupled components of an electrical stimulation system. For example, a retention assembly may be used to secure a lead or lead extension to a connector disposed on a control module (as shown in FIG. 3A) or a lead extension (as shown in FIG. 3B). Leads or lead extensions may also be secured to connectors disposed on other devices, such as an operating room cable or an adaptor. In FIG. 3A, the connector 144 is shown disposed on the control module 102. The connector 144 includes a connector housing 302. The connector housing 302 defines at least one port 304 into which a proximal end 306 of a lead or a lead extension 308 with terminals 310 can be inserted, as shown by directional arrow 312. The connector housing 302 also includes a plurality of connector contacts 314 and a fastener aperture 316 for each port 304. When the lead or the lead extension 308 is inserted into the port 304, the connector contacts 314 can be aligned with the terminals 310 on the lead or the lead extension 308 to electrically couple the control module 102 to the electrodes (134 of FIG. 1) electrically coupled to the lead or the lead extension 308. Examples of connectors in control modules are found in, for example, U.S. Pat. No. 7,244,150 and U.S. patent application Ser. No. 11/532,844, which are incorporated by reference.

In at least some embodiments, a retention assembly may be used to secure a lead or a lead extension to a connector disposed on a control module. In some embodiments, a retention assembly includes a fastener and a fastener aperture configured and arranged to mate with the fastener. For example, a fastener 318 can be mated with the fastener aperture 316 to form a retention assembly 320. The retention assembly 320 can be used to secure the lead or the lead extension 308 to the control module 102. Fasteners and fastener apertures can be made from many different metallic or ceramic materials suitable for implantation. In FIG. 3A, the fastener 318 is shown as a set screw and the fastener aperture 318 is shown as a threaded aperture configured and arranged to mate with the set screw. In at least some embodiments, the fastener 318 is inserted into the fastener aperture 316 and tightened against a retention sleeve 321 disposed on the lead or the lead extension 308 distal to the terminals 310. The retention sleeve 321 can be formed using any rigid, biocompatible material. Examples of suitable materials include metals, alloys, rigid polymers, rigid carbon, and the like, as well as combinations thereof. The fastener aperture 316 may be positioned in many different locations along the length of connector 144. In FIG. 3A and in subsequent figures, fastener apertures are shown disposed in proximity to the port 304 of the connector for clarity of illustration. Accordingly, the retention sleeve 321 is shown distal to the terminals 310 to align with the fastener aperture 316 when the proximal end 306 of the lead or the lead extension 308 is inserted into the port 304 of the connector 144.

In at least some embodiments, a retention assembly may be used to secure a lead or a lead extension to a connector disposed on a lead extension. In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead or a lead extension 334 with terminals 336 can be inserted, as shown by directional arrow 338. The connector housing 328 also includes a plurality of conductive contacts 340 and a fastener aperture 342. When the lead or the lead extension 334 is inserted into the port 330, the conductive contacts 340 disposed in the connector housing 328 can be aligned with the terminals 336 on the lead or the lead extension 334 to electrically couple the lead extension 324 to the electrodes (134 of FIG. 1) electrically coupled to the lead or the lead extension 334. A fastener 344 can be mated with the fastener aperture 342 to form a fastener assembly 346, which can be used to secure the lead or the lead extension 334 to the connector 322 disposed at the distal end 326 of the lead extension 324.

In at least some embodiments, the proximal end of a lead extension is similarly configured and arranged to a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. For example, in FIG. 3B the proximal end 348 of the lead extension 324 is inserted into a connector 350 disposed in a control module 352. A fastener 354 is disposed in a fastener aperture 356 and tightened against a retention sleeve 358 disposed on the lead extension 324 to secure the proximal end 348 of the lead extension 324 to the control module 348. Note that, when a lead or a lead extension includes two or more proximal ends, each proximal end can be inserted into one of a plurality of ports defined in a connector, with each port including a plurality of conductive contacts, and with each proximal end of the lead or the lead extension secured to the connector by one or more of the retention assemblies.

When a set screw and a corresponding threaded aperture are used to secure a lead or a lead extension to a connector, a tool, such as an Allen wrench, is sometimes used to tighten the set screw against a retention sleeve disposed on the lead or the lead extension, as shown in FIGS. 3A and 3B. Using a wrench, such as an Allen wrench, to tighten the set screw against the inserted lead or the lead extension can sometimes be burdensome and add additional time to a medical procedure. Consequently, it may be an advantage to utilize one or more retention assemblies that can be used to secure a lead or a lead extension to a connector without needing a wrench to facilitate the securement. It may especially be an advantage when the connector is disposed on a distal end of a lead extension. It may also be an advantage to utilize one or more retention assemblies to secure a lead or a lead extension to a connector without a wrench if an explant is to be performed and two or more components are to be separated and no appropriate wrench is readily available.

In at least some embodiments, a lead or a lead extension may be secured to a connector using a threaded member that mates with a threaded aperture. In at least some embodiments, a lead or a lead extension may be secured to a connector by a retention assembly incorporating a "screw-on" type of connection. FIG. 4 is a schematic longitudinal cross-sectional view of one embodiment of a connector 402 and a proximal end of a lead or a lead extension 404. The connector 402 has a proximal end 406 and a distal end 408 and includes a connector housing 410. The connector housing 410 defines a port 412 extending from the distal end 408 of the connector 402 and includes a plurality of connector contacts, such as connector contact 414, disposed in the connector housing 410. The connector housing 410 also includes a threaded post 416 disposed at the proximal end 406 of the connector 402.

The proximal end of the lead or the lead extension 404 includes a plurality of terminals, such as terminal 418, and defines a threaded aperture 420 proximal to the terminals that is configured and arranged to mate with the threaded post 416 when the proximal end of the lead or the lead extension 404 is inserted into the connector housing 410. The threaded post 416 can be mated with the threaded aperture 420 to form a retention assembly 422. In at least some embodiments, the threaded aperture 410 can be screwed onto the threaded post 416 without the need for a supplementary tool. In at least some embodiments, the proximal end of the lead or the lead extension 404 also defines at least one lumen 424 extending along a longitudinal length of the proximal end of the lead or the lead extension 404. In at least one embodiment, the threaded aperture 420 is continuous with the at least one lumen 424. In at least some embodiments, the threaded post 416 is disposed on the proximal end of the lead or the lead extension and the threaded aperture 420 is defined in the connector 402.

In at least some embodiments, a lead or a lead extension may be secured to a connector by a retention assembly incorporating a "pin vise" type of connection. FIG. 5 is a schematic longitudinal cross-sectional view of one embodiment of a connector 502 and a proximal end of a lead or a lead extension 504 inserted into the connector 502. The connector 502 has a proximal end 506 and a distal end 508 and includes a connector housing 510. The connector housing 510 includes a retention assembly 512. The retention assembly 512 includes a split collet 514 and a threaded collar 516. The split collet 514 includes one or more gripping members 518 disposed at the distal end 508 of the connector 502. In at least some embodiments, the one or more gripping members 518 serve as retention members. The threaded collar 516 is disposed over at least a portion of the split collet 514.

In at least some embodiments, the proximal end of the lead or the lead extension 504 includes a retention sleeve 520 disposed on the proximal end of the lead or the lead extension 504 distal to a plurality of terminals, such as terminal 522. When the proximal end of the lead or the lead extension 504 is inserted into the connector 502, the threaded collar 516 can be screwed in a proximal direction against the split collet 514. As the threaded collar 516 moves proximally down a longitudinal length of the connector 502, the one or more gripping members 518 are deformed inward, eventually pressing against the inserted proximal end of the lead or the lead extension 504 to secure the inserted proximal end of the lead or the lead extension 504 in the connector 502. In some embodiments, the one or more gripping members 518 press against an outer covering of the proximal end of the lead or the lead extension 504 distal to the plurality of terminals. In other embodiments, the one or more gripping members 518 press against an outer covering of the proximal end of the lead or the lead extension 504 proximal to the plurality of terminals. In at least some embodiments, the one or more gripping members 518 press against the retention sleeve 520 disposed on the proximal end of the lead or the lead extension 504, as shown in FIG. 5. In at least some embodiments, the retention sleeve 520 is a rigid portion of the lead, or a rigid element, such as a metal ring disposed on the lead, which may be used to provide a bearing for a fastener to tighten against. In at least some embodiments, the retention sleeve 520 is flush with an outer diameter of the lead or the lead extension 504.

In at least some embodiments, a lead or a lead extension may be secured to a connector by a retention assembly incorporating a "lockable latch" type of connection. FIG. 6 is a schematic side view of one embodiment of a connector 602 and a proximal end of a lead or a lead extension 604 inserted in the connector 602. In FIG. 6, a portion of the connector 602 is removed to show a longitudinal cross-sectional view of a portion of the connector 602 and the inserted proximal end of the lead or the lead extension 604. The connector 602 has a proximal end 606 and a distal end 608 and includes a connector housing 610. The connector housing 610 includes a retention assembly 612 which, in turn, includes one or more lockable latches 614 which serve as one or more retention members.

The one or more lockable latches 614 each include a hinged locking member 616 configured and arranged to pivot between an open position and a closed position. When each hinged locking member 616 is in an open position, as shown in FIG. 6 by the dashed representation 618 of the hinged locking member 616, the proximal end of the lead or the lead extension 604 can be inserted into, or removed from, the connector housing 610. The hinged locking member 616 can be pivoted to a closed position, as shown in FIG. 6 by the solid representation of the hinged locking member 616, to lock against a catch 620. When the proximal end of the lead or the lead extension 604 is inserted into the connector housing 610 and the hinged locking member 616 is locked against the catch 620, protrusions 622 disposed on the hinged locking member 616 and the catch 620 press against the inserted proximal end of the lead or the lead extension 604 to secure the lead or the lead extension 604 in the connector housing 610. In some embodiments, the protrusions 622 press against an outer surface of the proximal end of the lead or the lead extension 604 distal to the plurality of terminals. In some embodiments, the protrusions 622 press against an outer covering of the proximal end of the lead or the lead extension 604 distal to a retention sleeve 624 disposed on the proximal end of the lead or the lead extension 604, as shown in FIG. 6. In at least one embodiment, each of the one or more lockable latches can be pivoted from an open position to a closed position, and vice versa, by hand without the use of a supplementary tool. In at least some embodiments, one or more tools, such as forceps, can be used to pivot one or more of the lockable latches between an open and a closed position. In at least some embodiments, the locking member slides between an open and closed position. In some embodiments, the protrusions 622 are disposed on both the locking member 616 and the catch 620. In other embodiments, the protrusions are disposed on either the locking member 616 or the catch 620. In at least some embodiments, a plurality of protrusions 620 are disposed on either or both the locking member 616 or the catch 620.

In at least some embodiments, a lead or a lead extension may be secured to a connector by a retention assembly incorporating a "split shell" type of connection. FIG. 7A is a schematic perspective view of one embodiment of a connector 702 and a proximal end of a lead or a lead extension 704. The connector 702 has a proximal end 706, a distal end 708, and a longitudinal length, shown in FIG. 7A as a two-headed arrow 710. The connector 702 includes a connector housing 712. In at least some embodiments, the connector housing 712 is openable approximately longitudinally along the longitudinal length 710 of the connector housing 712 and includes a first piece 714 and a second piece 716. The first piece 714 including a first pocket 718 and the second piece 716 including a second pocket 720. The first pocket 718 including a plurality of connector contacts, such as connector contact 722. In at least some embodiments, the second pocket 720 also includes a plurality of connector contacts, such as connector contact 724. In FIG. 7A, the connector housing 712 is shown in an open position. In at least some embodiments, the connector housing 712 can be placed in a closed position by pivoting the second piece 716, as shown by directional arrow 726, to form a retention assembly 728. In some embodiments, the first piece 714 and the second piece 716 are coupled to one another by one or more pivots. For example, as shown in FIG. 7A, one or more hinges may couple the first piece 714 to the second piece 716. In other embodiments, the first piece 714 and the second piece 716 may be separate pieces that couple together by one or more fasteners. Many different types of fasteners may be used, including, adhesive, one or more snaps, one or more clasps, and the like or combinations thereof. For example, the first piece 714 and the second piece 716 may snap together. In at least some embodiments, the retention assembly may employ both one or more pivots and one or more fasteners.

The proximal end of the lead or the lead extension 704 includes a plurality of terminals, such as terminal 730, disposed at the proximal end of the lead or the lead extension 704. The proximal end of the lead or the lead extension 704 also includes an annular groove 732 proximal to the plurality of terminals and a proximal flange 734 disposed proximal to the annular groove 732. The annular groove 732 may have many different widths and depths. Additionally, the annular groove 732 may have many different longitudinal cross-sectional shapes. For example, the annular groove 732 may have a longitudinal cross-sectional shape that is U-shaped, V-shaped, hemispherical-shaped, W-shaped, rectangular-shaped, and the like. In at least some embodiments, the annular groove 732 is positioned proximal to the plurality of terminals. In at least some embodiments, the annular groove 732 is positioned in a retention sleeve, such as the retention sleeve (321 in FIG. 3A, 520 in FIG. 5, and 624 in FIG. 6).

In at least some embodiments, the first pocket 718 and the second pocket 720 are configured and arranged to collectively approximate the shape of the proximal end of the lead or the lead extension 704 when the proximal end of the lead or the lead extension 704 is inserted into the connector 702 and the connector housing 712 is pivoted to a closed position. In at least some embodiments, the shape of the annular groove 732 facilitates securement of the inserted lead or the lead extension 704 in the connector housing 712 when the connector housing 712 is in a closed position. In at least some embodiments, the shape of the annular groove 732 and the proximal flange 734 facilitate securement of the inserted lead or the lead extension 704 in the connector housing 712 when the connector housing 712 is in a closed position.

Figure 7B:
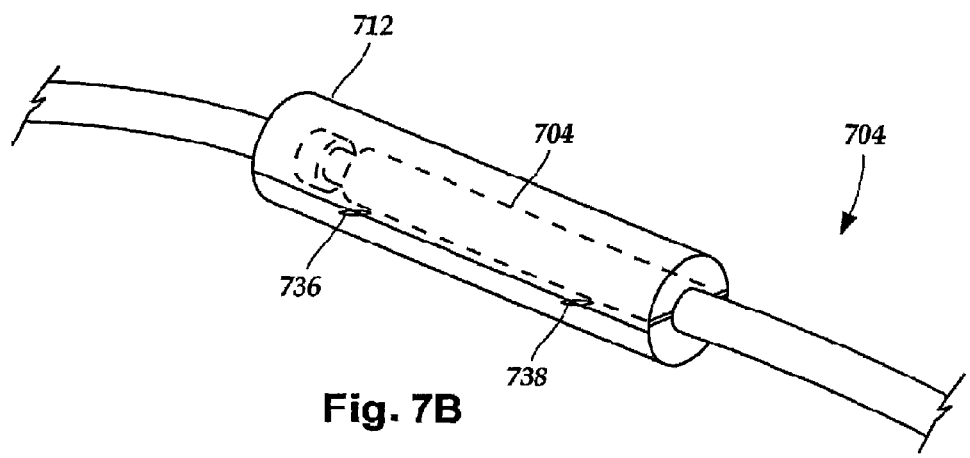
FIG. 7B is a schematic perspective view of one embodiment of the proximal end of the lead or the lead extension shown in FIG. 7A inserted into the connector shown in FIG. 7A, the connector maintained in a closed position by snap-fit closures, according to the invention.
Figure 7C:
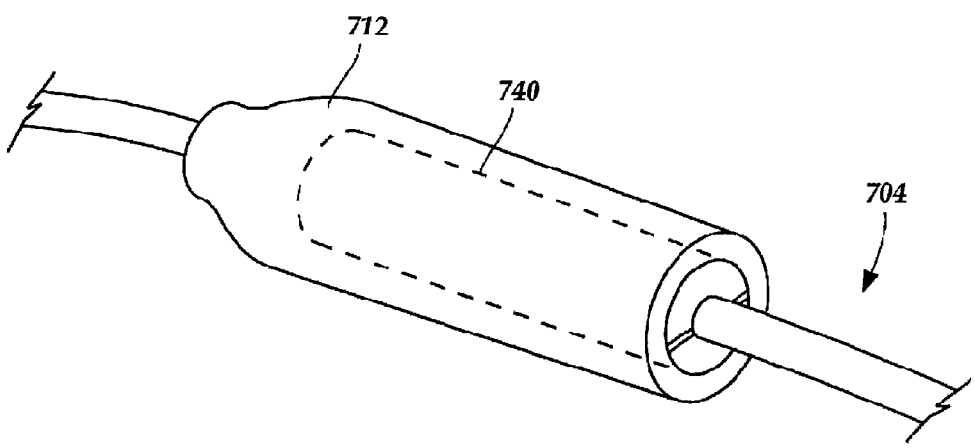
FIG. 7C is a schematic perspective view of one embodiment of the proximal end of the lead or the lead extension shown in FIG. 7A inserted into the connector shown in FIG. 7A, the connector maintained in a closed position by a cylindrical sleeve disposed over the connector, according to the invention.

In some embodiments, the connector housing 712 is maintained in a closed position by one or more closures, such as snap-fit closures, disposed on the first piece 714 and the second piece 716. FIG. 7B is a schematic perspective view of one embodiment of the proximal end of the lead or the lead extension 704 inserted into the connector housing 712 and the connector housing 712 maintained in a closed position by snap-fit closures 736 and 738. In other embodiments, the connector housing 712 is maintained in a closed position by a cylindrical sleeve disposed over at least a portion of the connector housing 712. FIG. 7C is a schematic perspective view of one embodiment of the proximal end of the lead or the lead extension 704 inserted into the connector housing 712 and the connector housing 712 maintained in a closed position by a cylindrical sleeve 740 disposed over at least a portion of the connector housing 712.

Figure 8A:
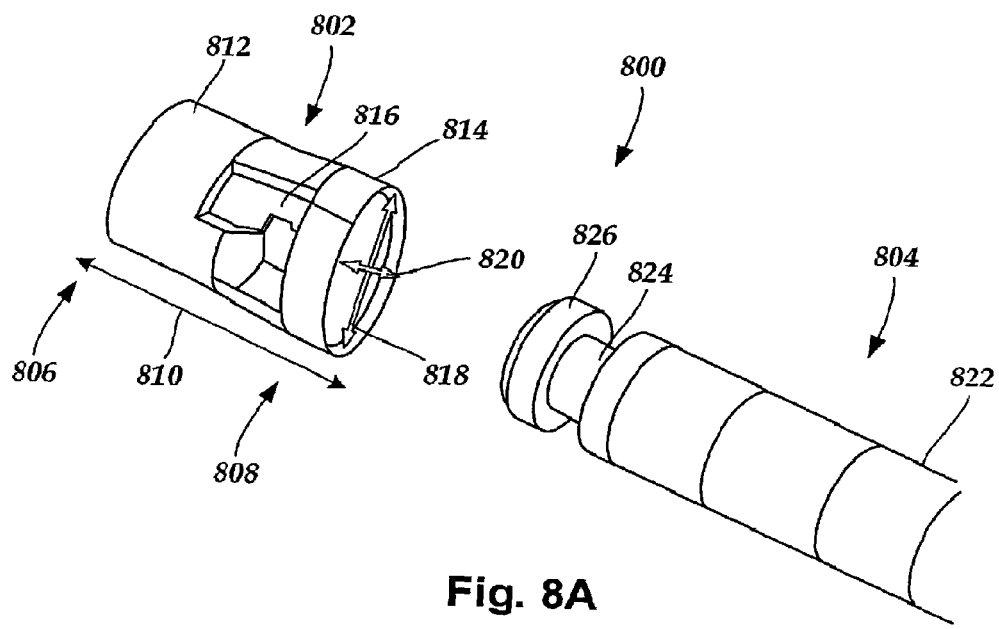
FIG. 8A is a schematic perspective view of one embodiment of a retention assembly that includes a clip configured and arranged to be mounted to a connector and a proximal end of a lead or a lead extension configured and arranged for insertion into the clip, according to the invention.
Figure 8B:
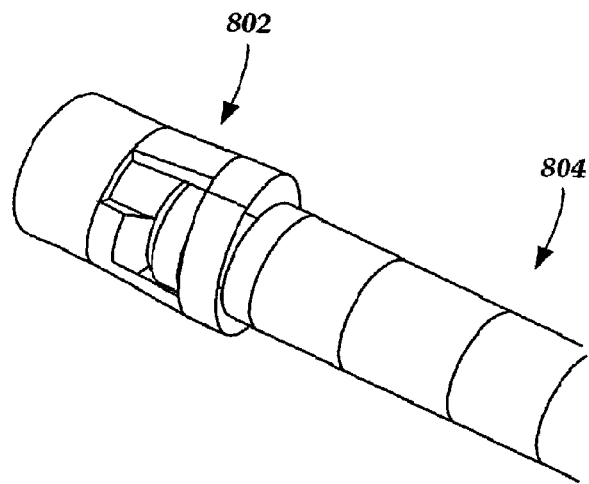
FIG. 8B is a schematic perspective view of one embodiment of the proximal end of the lead or the lead extension shown in FIG. 8A secured in the clip shown in FIG. 8A, according to the invention.

In at least some embodiments, a lead or a lead extension may be secured to a connector by a retention assembly incorporating a "deformable member" type of connection. FIG. 8A is a schematic perspective view of one embodiment of a retention assembly 800. The retention system 800 includes a clip 802 configured and arranged to be mounted to a proximal end of a connector (see e.g., 144 of FIGS. 2 and 3A, and 322 and 350 of FIG. 3B) and a proximal end of a lead or a lead extension 804 configured and arranged for insertion into the clip 802. In FIGS. 8A-8B, the connector has been omitted for clarity of illustration.

In at least some embodiments, the clip 802 has a proximal end 806, a distal end 808, and a longitudinal length 810. The clip 802 includes a base 812 at the proximal end 806 and one or more deformable circumferential members 814 forming an elongated opening, such as an oval-shaped opening, at the distal end 808. In at least some embodiments, the clip 802 also defines at least one window 816 along the longitudinal length 810 of the clip 802. The elongated opening is formed by the one or more deformable circumferential members 814 at the distal end 808. The elongated opening includes a major axis 818 and a minor axis 820. The proximal end of the lead or the lead extension 804 includes a plurality of terminals, such as terminal 822, disposed at the proximal end of the lead or the lead extension 804. The proximal end of the lead or the lead extension 804 also includes an annular groove 824 proximal to the plurality of terminals and a proximal flange 826 disposed proximal to the annular groove 824.

In at least some embodiments, the clip 802 is configured and arranged to receive the proximal end of the lead or the lead extension 804 through the elongated opening formed by the one or more deformable circumferential members 814. In some embodiments, the one or more deformable circumferential members 814 are chamfered along at least a portion of the distal end of the one or more deformable circumferential members 814 to facilitate insertion of the proximal end of the lead or the lead extension into the elongated opening. Likewise, in some embodiments the proximal end of the proximal flange 826 is chamfered along at least a portion of a circumference of the proximal end of the proximal flange 826 to facilitate insertion of the proximal end of the lead or the lead extension into the elongated opening.

In at least some embodiments, the proximal end of the lead or the lead extension 804 may be inserted into the clip 802 by squeezing the one or more deformable circumferential members 814 in proximity to one or more ends of the major axis 818 to deform the one or more deformable circumferential members 814 into an approximately round shape. When the one or more deformable circumferential members 814 are deformed into an approximately round shape, the proximal end of the lead or the lead extension 804 may be disposed into the clip 802. Once the proximal end of the lead or the lead extension 804 is at least partially inserted into the clip 802 and the squeezing is ceased, the one or more deformable circumferential members 814 reform to an elongated shape and the minor axis 820 of the one or more deformable circumferential members 814 press against the proximal end of the lead or the lead extension 804.

In at least some embodiments, the proximal end of the lead or the lead extension 804 may be disposed in the clip 802 by application of a compressive force between the proximal end of the lead or the lead extension 804 and the clip 802. For example, in some embodiments, a force may be applied to the proximal end of the lead or the lead extension 804 while pressed against the elongated opening of the clip 802 to deform the elongated opening of the clip 802 and allow passage of the proximal end of the lead or the lead extension 804 into the clip 802. In other embodiments, a force may be applied to the clip 802 while the elongated opening of the clip 802 is pressed against the proximal end of the lead or the lead extension 804 to deform the elongated opening of the clip 802 and allow passage of the proximal end of the lead or the lead extension 804 into the clip 802. In at least some embodiments, insertion of the proximal end of the lead or the lead extension 804 into the elongated opening may be facilitated by the chamfered proximal flange 826. In at least some embodiments, the proximal end of the lead or the lead extension 804 may be inserted into the clip 802 by both squeezing the one or more deformable circumferential members 814 and applying a compressive force between the clip 802 and the proximal end of the lead or the lead extension 804 when the proximal end of the lead or the lead extension 804 is pressed against the elongated opening.

In at least some embodiments, the clip 802 is configured and arranged so that when the proximal end of the lead or the lead extension 804 is fully inserted into the clip 802, the proximal flange 826 rests against the base 812 and the portions of the one or more deformable circumferential members 814, on or in proximity to, the minor axis 820 of the elongated opening engage the annular groove 824 and secure the proximal end of the lead or the lead extension to the clip 802.

In at least some embodiments, a signal, such as an audible sound or a tactile signal, is emitted when the one or more deformable circumferential members 814 engage the annular groove 824 of the proximal end of the lead or the lead extension 804. For example, in one embodiment the one or more deformable circumferential members 814 "snap" when the one or more deformable circumferential members 814 engage the annular groove 824. FIG. 8B is a schematic perspective view of one embodiment of the proximal end of the lead or the lead extension 804 secured in the clip 802.

The clip 802 can be formed using any high-strength, biocompatible material suitable for mounting to a connector of an electrical stimulation system. Examples of suitable materials include plastic resins such as PEEK, hard polyurethane, polycarbonate, or other high-strength plastic resins, as well as other high-strength materials, such as stainless steel, titanium, ceramics, and the like, as well as combinations thereof. The clip 802 may be formed in the desired shape by any process including, for example, stamping, molding (including injection molding), casting, and the like. In at preferred embodiments, the clip 802 is formed by stamping stainless steel or titanium from a progressive die.

Figure 9C:
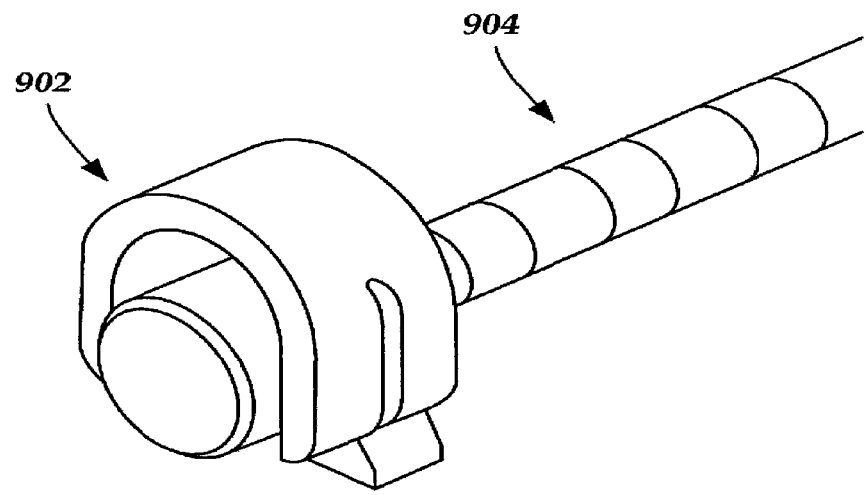
FIG. 9C is a schematic perspective view of one embodiment of the proximal end of the lead or the lead extension shown in FIGS. 9A and 9B secured in the sliding lock shown in FIG. 9A in a retaining position, according to the invention.

In at least some embodiments, a lead or a lead extension may be secured to a connector by a retention assembly incorporating a "slider" type of connection. FIG. 9A is a schematic perspective view of another embodiment of a retention assembly 900. The retention assembly 900 includes a sliding lock 902 configured and arranged to be mounted to a proximal end of a connector (see e.g., 144 of FIGS. 2 and 3A, and 322 and 350 of FIG. 3B) and a proximal end of a lead or a lead extension 904 configured and arranged for insertion into the sliding lock 902. In FIGS. 9A-9D, the connector has been omitted for clarity of illustration. The sliding lock 902 includes a housing 906 and an attached slider 908. In at least some embodiments, the housing 906 defines an insertion port 910 configured and arranged for receiving the proximal end of the lead or the lead extension 904. The housing 906 also includes one or more ramps 912 and 914 disposed on one side of the insertion port 910.

In at least some embodiments, the slider 908 has a horseshoe shape and includes two ends 916 and 918 that slide against the housing 906 in a direction indicated by directional arrow 920. The slider 908 also includes a cross-bar 922 coupled to each of the two ends 916 and 918 of the slider 908. In at least some embodiments, the slider 908 is configured and arranged to control passage of the proximal end of the lead or the lead extension in and out of the insertion port 910 by sliding between an open position and a retaining position. In FIG. 9A, the multi-piece element 902 is shown in a retaining position. In a retaining position, the cross-bar 922 extends partially into the insertion port 910. In at least some embodiments, when the slider 908 is slid in the direction indicated by directional arrow 920, the amount of the cross-bar 922 extending into the insertion port 910 decreases, until eventually the cross-bar 922 does not extend into the insertion port 910, at which point the sliding lock 902 is in an open position and may receive the proximal end of the lead or the lead extension 904.

In at least some embodiments, the sliding lock 902 is maintained in the retaining position by a cantilever spring embodied by the slider 908. When the sliding lock 902 is in the retaining position, as shown in FIG. 9A, the ends 916 and 918 of the slider 908 rest against an outer surface of the housing 906 superior to the one or more ramps 912 and 914 disposed on the housing 906. When the slider 908 is slid in the direction indicated by the directional arrow 920 into an open position, one or more of the ends 916 and 918 slide along the one or more ramps 912 and 914, causing one or more of the ends 916 and 918 to deform and separate from one another. In at least some embodiments, additional amounts of force are needed to slide the slider 908 in the direction indicated by the directional arrow 920 as the distance between the ends 916 and 918 of the slider 908 increases. Thus, in at least some embodiments, when the force applied to the slider 908 is ceased, the slider 908 slides in a direction opposite to the direction indicated by the directional arrow 920 and the sliding lock 902 returns to a retained position.

In at least some embodiments, one or more of the ends 916 and 918 of the slider 908 include a vertical slit, such as vertical slit 924, dividing the end 918 into a proximal portion and a distal portion, such as proximal portion 926 and distal portion 928. In at least some embodiments, the cross-bar 922 is attached to the proximal portions of each end 916 and 918 the distal portions of the ends 916 and 918 are configured and arranged to slide along the one or more ramps 912 and 914. Thus, in at least some embodiments, the distal portions of the ends 916 and 918 of the slider 908 can deform against the ramps 912 and 914 without stretching the cross-bar 922. The proximal end of the lead of the lead extension 904 includes a plurality of terminals, such as terminal 936, disposed at the proximal end of the lead or the lead extension 904. The proximal end of the lead or the lead extension 904 also includes an annular groove 938 proximal to the plurality of terminals.

FIG. 9B is a schematic perspective view of one embodiment of the sliding lock 902 in an open position. In at least some embodiments, as shown in FIG. 9B, the distal portions of the ends 916 and 918 are deformed outward in directions indicated by directional arrows 930 and 932, respectively, as the distal portions of the ends 916 and 918 slide along the ramps 912 and 914, respectively. The insertion port 910 is unobstructed and the proximal end of the lead or the lead extension 904 can be inserted into the insertion port 910 of the sliding lock 902, as shown by directional arrow 934. The proximal end of the lead of the lead extension 904 includes a plurality of terminals, such as the terminal 936, disposed at the proximal end of the lead or the lead extension 904. The proximal end of the lead or the lead extension 904 also includes the annular groove 938 proximal to the plurality of terminals In at least some embodiments, once the proximal end of the lead or the lead extension is inserted into the sliding lock 902, the force applied to the slider 908 can be ceased, causing the slider 908 to return to the retaining position, thereby securing the proximal end of the lead or the lead extension 904 in the sliding lock 902. In at least some embodiments, application of force may not be needed to maintain the slider 908 in an open position. In at least some embodiments, a friction force may be employed to maintain the slider 908 in an open position. FIG. 9C is a schematic perspective view of one embodiment of the proximal end of the lead or the lead extension 904 secured in the sliding lock 902.

Figure 9D:
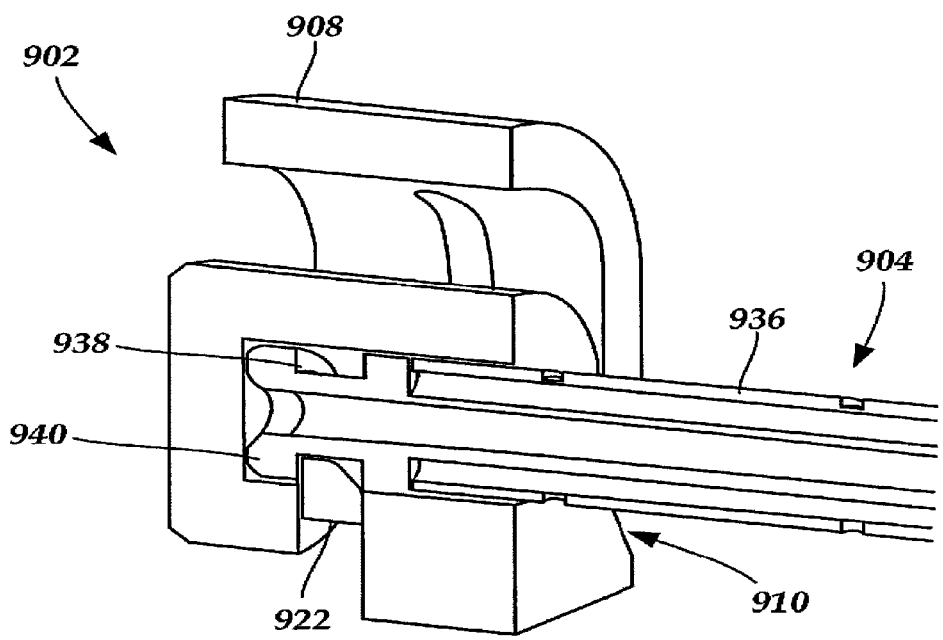
FIG. 9D is a schematic perspective, longitudinal cross-sectional view of one embodiment of the proximal end of the lead or the lead extension shown in FIGS. 9A and 9B secured in the sliding lock shown in FIGS. 9A and 9B placed in a retaining position, according to the invention.

In at least some embodiments, the cross-bar 922 is configured and arranged to engage the annular groove 938 disposed on the proximal end of the lead or the lead extension 904. FIG. 9D is a schematic perspective, longitudinal cross-sectional view of one embodiment of the proximal end of the lead or the lead extension 904 secured in the sliding lock 902 while the sliding lock 902 is in a retaining position. The proximal end of the lead of the lead extension 904 includes a plurality of terminals, such as the terminal 936, the annular groove 938, and the proximal flange 940. In at least some embodiments, when the proximal end of the lead or the lead extension is fully inserted into the insertion port 910 and the slider 908 is released to secure the proximal end of the lead or the lead extension 904, the cross-bar 922 is configured and arranged to engage the annular groove 932 of the proximal end of the lead or the lead extension 904. In at least some embodiments, a signal, such as an audio signal or a tactile signal, is emitted when the cross-bar 922 engages the annular groove 938 of the proximal end of the lead or the lead extension 904. For example, in one embodiment the cross-bar 922 "snaps" when the cross-bar 922 engages the annular groove 938.

The sliding lock 902 can be formed using any high-strength, biocompatible material suitable for mounting to a connector of an electrical stimulation system. Examples of suitable materials include plastic resins such as PEEK, hard polyurethane, polycarbonate, or other high-strength plastic resins, as well as other high-strength materials, such as stainless steel, ceramics, and the like, as well as combinations thereof. The sliding lock 902 may be formed in the desired shape by any process including, for example, molding (including injection molding), casting, and the like. In a preferred embodiments, the sliding lock 902 is formed from plastic.

Figure 10:
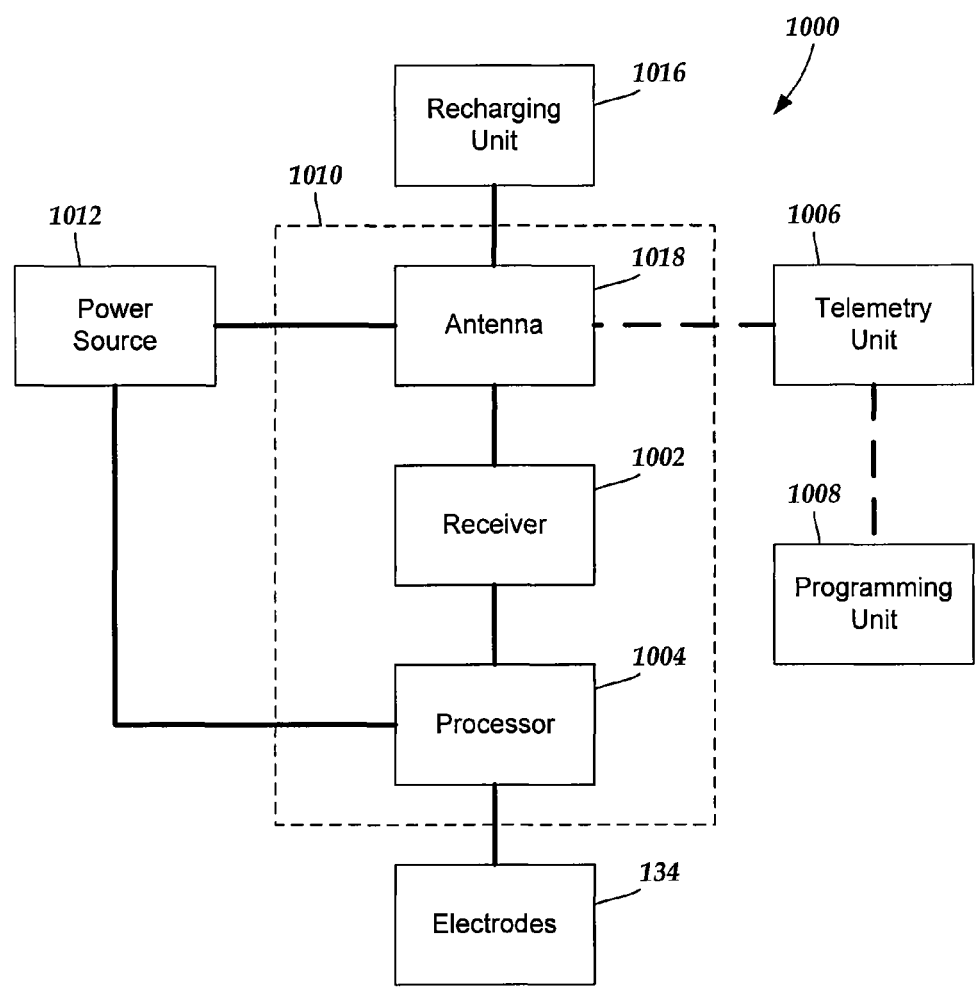
FIG. 10 is a schematic overview of one embodiment of components of a stimulation system, including an electronic subassembly disposed within a control module, according to the invention.

FIG. 10 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, power source 1012, antenna 1018, receiver 1002, and processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrodes can be used to provide stimulation, if desired. In some embodiments, the processor 1004 may select which electrode(s) are cathodes and which electrode(s) are anodes. In some embodiments, the processor 1004 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by a programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include an antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A connector assembly comprising:
   a lead or a lead extension with a proximal end, the lead or the lead extension comprising
   a plurality of terminals disposed along the proximal end of the lead or the lead extension,
   an annular groove disposed along the proximal end of the lead or the lead extension, the annular groove having a diameter;
   a flange disposed along the proximal end of the lead or the lead extension, the flange having a diameter that is larger than the diameter of the annular groove, wherein the flange is disposed along the proximal end of the lead or the lead extension proximal to the annular groove; and
   a connector with a proximal end, a distal end, and a longitudinal length, the connector configured and arranged to receive the lead or the lead extension, the connector comprising
   a connector housing defining a port at the distal end of the connector, the port configured and arranged for receiving the proximal end of the lead or the lead extension,
   a plurality of connector contacts disposed in the connector housing, the connector contacts configured and arranged to couple to at least one of the plurality of terminals disposed on the proximal end of the lead or the lead extension, and
   a retention assembly configured and arranged for removably securing the lead or the lead extension to the connector, the retention assembly comprising a coupling member disposed on the connector, the coupling member configured and arranged to couple with the annular groove disposed in the lead or the lead extension.

2. The connector assembly of claim 1, wherein the retention assembly comprises a split shell connector housing, the split shell connector housing comprising a first piece and a second piece attachable to the first piece, the first piece defining a first pocket and the second piece defining a second pocket.

3. The connector assembly of claim 2, wherein the first pocket and the second pocket collectively approximate the shape of the proximal end of the lead or the lead extension, a portion of the first pocket and the second pocket approximating the shape of the annular groove and blocking the removal of the proximal end of the lead or the lead extension from the split shell connector housing when the proximal end of the lead or the lead extension is inserted into the split shell connector housing and the first piece is attached to the second piece.

4. The connector assembly of claim 1, wherein the connector housing comprises a clip configured and arranged to couple to the proximal end of the connector, the clip having a proximal end, a distal end, and a longitudinal length, the clip comprising a base disposed at the proximal end of the clip, at least one deformable circumferential member forming an elongated opening at the distal end of the clip; and at least one window defined in the longitudinal length of the clip.

5. The connector assembly of claim 4, wherein the elongated opening formed by the at least one deformable circumferential member comprises a major axis and a minor axis, the elongated opening configured and arranged to receive the proximal end of the lead or the lead extension when at least one portion of the at least one deformable circumferential member in proximity to an end of the major axis of the elongated opening is pressed to deform the at least one deformable circumferential member into an approximately round shape to receive the proximal end of the lead or the lead extension.

6. The connector assembly of claim 5, wherein the at least one deformable circumferential member is configured and arranged to reform to an elongated shape when the medially-directed pressing of the at least one deformable circumferential member is ceased, the reforming of the at least one deformable circumferential member to an elongated shape configured and arranged to engage the annular groove of the lead or the lead extension when the lead or the lead extension is inserted into the clip.

7. The connector assembly of claim 6, wherein the at least one deformable circumferential member is configured and arranged to emit one or more audible or tactile signals when the at least one deformable circumferential member reforms to an elongated shape and engages the annular groove of the proximal end of the lead or the lead extension.

8. The connector assembly of claim 1, wherein the retention assembly comprises:

a sliding lock configured and arranged for coupling to the proximal end of the connector, the sliding lock comprising a housing defining an insertion port and at least one ramp, the insertion port configured and arranged for receiving the proximal end of the lead or the lead extension; and a slider attached to the housing, the slider having two ends disposed at opposing ends of the housing superior to the at least one ramp, the sliding element comprising a cross-bar coupling the two ends of the sliding element, the slider configured and arranged to slide between an open position and a retaining position, the open position configured and arranged to facilitate insertion of the lead or the lead extension into the insertion port of the housing and the retaining position configured and arranged to engage the annular groove of the lead or the lead extension when the lead or the lead extension is inserted into the sliding lock.

9. The connector assembly of claim 8, wherein the two ends of the slider are configured and arranged to slide from the retaining position to the open position when a force is applied to the slider to slide at least one of the two ends over the at least one ramp, thereby deforming at least one of the two ends of the slider so that the slider returns to a retaining position when the force applied to the slider is ceased.

10. The connector assembly of claim 9, wherein the slider defines a vertical slit at each of the two ends, the vertical slit dividing each of the two ends into a proximal portion and a distal portion, the cross-bar coupled to the proximal portion of each of the two ends, and the distal portion of at least one of the two ends is slidable on the at least one ramp.

11. The connector assembly of claim 8, wherein the cross-bar is configured and arranged to emit one or more audible or tactile signals when the cross-bar engages the annular groove of the proximal end of the lead or the lead extension.

* * * * *